(12) United States Patent
Zhang et al.

(10) Patent No.: US 9,572,540 B2
(45) Date of Patent: Feb. 21, 2017

(54) CT SYSTEM AND DETECTION DEVICE FOR CT SYSTEM

(71) Applicants: NUCTECH COMPANY LIMITED, Beijing (CN); TSINGHUA UNIVERSITY, Beijing (CN)

(72) Inventors: Li Zhang, Beijing (CN); Zhiqiang Chen, Beijing (CN); Yuanjing Li, Beijing (CN); Mingliang Li, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 14/355,175

(22) PCT Filed: Jul. 15, 2013

(86) PCT No.: PCT/CN2013/079382
§ 371 (c)(1),
(2) Date: Apr. 29, 2014

(87) PCT Pub. No.: WO2014/048163
PCT Pub. Date: Apr. 3, 2014

(65) Prior Publication Data
US 2014/0270058 A1    Sep. 18, 2014

(30) Foreign Application Priority Data

Sep. 26, 2012 (CN) .......................... 2012 1 0364118

(51) Int. Cl.
*G01T 1/24* (2006.01)
*H01L 27/146* (2006.01)
(Continued)

(52) U.S. Cl.
CPC ............ *A61B 6/482* (2013.01); *A61B 6/4241* (2013.01); *G01T 1/242* (2013.01);
(Continued)

(58) Field of Classification Search
CPC ....... A61B 6/032; A61B 6/4035; A61B 6/405; A61B 6/4241; A61B 6/583; A61B 6/4441; A61B 6/505; A61B 6/06; A61B 6/4488; A61B 6/542; A61B 6/027; A61B 6/0421; A61B 6/4042; A61B 6/4225; A61B 6/4233; A61B 6/4405; A61B 6/00; A61B 6/02; A61B 6/03; A61B 6/035; A61B 6/04;A61B 6/0407; A61B 6/0457; A61B 6/42; A61B 6/4208; A61B 6/4266; A61B 6/44; A61B 6/48; A61B 6/482; A61B 6/54; G01T 1/00; G01T 1/16; G01T 1/1603; G01T 1/2017; G01T 1/24; G01T 1/242; G01T 1/243; G01T 1/36; G01T 1/361; G01T 1/362; G01T 1/366; H01L 25/00; H01L 25/03; H01L 25/04; H01L 25/065; H01L 25/0652; H01L 25/0657; H01L 25/10; H01L 25/105; H01L 25/18; H01L 27/00; H01L 27/14; H01L 27/142; H01L 27/144; H01L 27/1446; H01L 27/146; H01L 27/14601; H01L 27/14618; H01L 27/1462; H01L 27/14623; H01L 27/14634; H01L 27/14643; H01L 27/14658; H01L 27/14665; H01L 27/14676; H01L 27/14806; H01L 27/14812; H01L 27/14818; H01L 27/14831
(Continued)

(56) References Cited

U.S. PATENT DOCUMENTS 5,742,660 A    4/1998    Majewski et al.
6,418,189 B1   7/2002    Schafer
(Continued)

FOREIGN PATENT DOCUMENTS

CN    1319759 A    10/2001
CN    101470086 A    7/2009
(Continued)

OTHER PUBLICATIONS

State Intellectual Property Office of the People's Republic of China, International Search Report in International Application No. PCT/CN2013/079382 (Oct. 24, 2013).
(Continued)

*Primary Examiner* — Anastasia Midkiff
(74) *Attorney, Agent, or Firm* — Leydig, Voit & Mayer, Ltd.

(57) ABSTRACT

A detection device for a CT system comprises a low-energy detector assembly; and a high-energy detector assembly disposed under the low-energy detector assembly. The high-
(Continued)

energy detector assembly comprises: a plurality of rows of high-energy detectors arranged at predetermined intervals. With the detection device, detectors and data acquisition units are greatly reduced. A high-resolution three-dimensional CT image is acquired while high-accuracy hazardous article alarm is achieved. The cost of manufacture of the system is greatly decreased while high system performance is ensured.

20 Claims, 3 Drawing Sheets

(51) Int. Cl.
*H01L 27/148* (2006.01)
*A61B 6/00* (2006.01)
*A61B 6/04* (2006.01)
*G01N 23/04* (2006.01)
*G01V 5/00* (2006.01)

(52) U.S. Cl.
CPC .. *H01L 27/14634* (2013.01); *H01L 27/14658* (2013.01); *H01L 27/14676* (2013.01); *H01L 27/14812* (2013.01); *A61B 6/0457* (2013.01); *A61B 6/542* (2013.01); *G01N 23/046* (2013.01); *G01N 2223/419* (2013.01); *G01N 2223/643* (2013.01); *G01V 5/0041* (2013.01); *H01L 27/14601* (2013.01); *H01L 27/14806* (2013.01)

(58) Field of Classification Search
USPC .............................................. 378/4, 9, 15, 62
See application file for complete search history.

(56) References Cited

U.S. PATENT DOCUMENTS

| | | | |
|---|---|---|---|
| 6,445,765 B1 | 9/2002 | Frank et al. | |
| 7,103,137 B2 | 9/2006 | Seppi et al. | |
| 7,369,640 B2 | 5/2008 | Seppi et al. | |
| 7,672,422 B2 | 3/2010 | Seppi et al. | |
| 7,724,869 B2 | 5/2010 | Wang et al. | |
| 7,852,981 B2 | 12/2010 | Luo et al. | |
| 8,488,736 B2 | 7/2013 | Hoffman et al. | |
| 2002/0190214 A1* | 12/2002 | Wieczorek | G01T 1/202 250/367 |
| 2004/0017888 A1 | 1/2004 | Seppi et al. | |
| 2006/0274879 A1 | 12/2006 | Ellenbogen et al. | |
| 2007/0003003 A1 | 1/2007 | Seppi et al. | |
| 2007/0286337 A1 | 12/2007 | Wang et al. | |
| 2008/0205583 A1 | 8/2008 | Seppi et al. | |
| 2009/0110143 A1 | 4/2009 | Zhang et al. | |
| 2009/0168948 A1 | 7/2009 | Luo et al. | |
| 2009/0283682 A1 | 11/2009 | Star-Lack et al. | |
| 2010/0002834 A1 | 1/2010 | Gudmundson et al. | |
| 2011/0080995 A1 | 4/2011 | Hoffman et al. | |
| 2012/0140874 A1 | 6/2012 | Li et al. | |
| 2012/0145911 A1 | 6/2012 | Suyama | |
| 2014/0037045 A1* | 2/2014 | Dafni | A61B 6/032 378/5 |

FOREIGN PATENT DOCUMENTS

| | | |
|---|---|---|
| CN | 101897593 A | 12/2010 |
| CN | 101900694 A | 12/2010 |
| CN | 101937094 A | 1/2011 |
| CN | 202948145 U | 5/2013 |
| EP | 0 287 707 A2 | 10/1988 |
| EP | 1 186 909 A2 | 3/2002 |
| EP | 2 437 051 A1 | 4/2012 |
| JP | H07-043321 A | 2/1995 |
| JP | 2005-534009 A | 11/2005 |
| JP | 2007-309929 A | 11/2007 |
| JP | 2009-082250 A | 4/2009 |
| JP | 2009-109499 A | 5/2009 |
| JP | 2011-064640 A | 3/2011 |
| JP | 2012-073056 A | 4/2012 |
| JP | 2012-125573 A | 7/2012 |

OTHER PUBLICATIONS

State Intellectual Property Office of the People's Republic of China, Written Opinion in International Application No. PCT/CN2013/079382 (Oct. 24, 2013).
European Patent Office, Extended European Search Report in European Patent Application Mo. 13 84 0115 (Aug. 25, 2015).
State Intellectual Property Office of the People's Republic of China, Office Action in Chinese Patent Application No. 201210364118.3 (Nov. 3, 2015).
Intellectual Property Office of the People's Republic of Australia, Examination Report in Australian Patent Application No. 2013324945 (Jan. 20, 2016).
Japan Patent Office, Notification of Reasons for Refusal in Japanese Patent Application No. 2015-532280 (Feb. 23, 2016).
Korean Intellectual Property Office, Notification of Reason for Refusal in Korean Patent Application No. 10-2015-7010318 (Mar. 28, 2016).

* cited by examiner

CT SYSTEM AND DETECTION DEVICE FOR CT SYSTEM

CROSS-REFERENCE TO RELATED APPLICATIONS

This patent application is the U.S. national phase of International Application No. PCT/CN2013/079382, filed on Jul. 15, 2013, which claims the benefit of Chinese Patent Application No. 201210364118.3, filed Sep. 26, 2012, the disclosures of which are incorporated by reference.

BACKGROUND OF THE INVENTION

Field of the Invention

The present invention relates to a CT system and a detection device for the CT system.

Description of the Related Art

In order to solve the problem of a scanning speed of a CT system, in a conventional method, a surface-array detector is adopted so that data can be acquired in rows simultaneously every time to improve the scanning speed. With requirement for a high accuracy of identification of hazardous articles in the field of safety inspection, a demand for dual-energy technique becomes increasingly desirable. In order to achieve high-speed scan and a high-resolution three-dimensional dual-energy image, conventionally a surface-array arrangement is adopted in both a high-energy detector and a low-energy detector. Numbers of detectors and data acquisition units of such a system requires are enormous. As a result, the cost for manufacturing the system is too high.

SUMMARY OF THE INVENTION

It is an object of the present invention to provide a CT system and a detection device for the CT system, thereby reducing the cost while ensuring high performance of identification of hazardous articles.

In accordance with an aspect of the present invention, there is provided a detection device for a CT system. The detection device comprises a low-energy detector assembly; and a high-energy detector assembly disposed under the low-energy detector assembly, wherein the high-energy detector assembly comprises: a plurality of rows of high-energy detectors arranged at predetermined intervals.

In accordance with an aspect of the present invention, the detection device further comprises a filter disposed between the low-energy detector assembly and the high-energy detector assembly.

In accordance with an aspect of the present invention, the CT system transfers an object under inspection in a transfer direction, and the plurality of rows of high-energy detectors are arranged substantially in the transfer direction.

In accordance with an aspect of the present invention, the low-energy detector assembly comprises surface-array low-energy detectors.

In accordance with an aspect of the present invention, the surface-array low-energy detectors are distributed substantially on a circular cylindrical surface.

In accordance with an aspect of the present invention, a surface of each high-energy detector facing towards the low-energy detector assembly is located substantially in a circular cylindrical surface.

In accordance with an aspect of the present invention, the predetermined intervals are from 5 mm to 80 mm.

In accordance with an aspect of the present invention, the predetermined intervals are from 30 mm to 50 mm.

In accordance with an aspect of the present invention, the detection device further comprises a member disposed between adjacent ones of the high-energy detectors.

In accordance with an aspect of the present invention, the member is made of a ray absorption material.

In accordance with an aspect of the present invention, the member is made of at least one of aluminum, iron, copper and lead, or an alloy of at least one of aluminum, iron, copper and lead.

In accordance with an aspect of the present invention, the high-energy detector assembly, and some low-energy detectors, superposed on the high-energy detectors of the high-energy detector assembly, of low-energy detectors of the low-energy detector assembly are configured to acquire a dual-energy CT image.

In accordance with another aspect of the present invention, there is provided a CT system. The CT system comprises a transfer device for transferring an object under inspection in a transfer direction; a gantry; a ray source connected to the gantry; and a detection device connected to the gantry opposite the ray source, wherein the detection device comprises a low-energy detector assembly; and a high-energy detector assembly disposed under the low-energy detector assembly, wherein the high-energy detector assembly comprises: a plurality of rows of high-energy detectors arranged at predetermined intervals.

In accordance with an aspect of the present invention, the plurality of rows of high-energy detectors are arranged substantially in the transfer direction.

In accordance with an aspect of the present invention, every time the gantry rotates through 360/N degrees, an object under inspection is moved by means of the transfer device by a distance equal to a distance between centers of adjacent ones of the plurality of rows of high-energy detectors, where N is a number of rows of the high-energy detectors.

In accordance with an aspect of the present invention, every time the gantry rotates through 360/N degrees, an object under inspection is moved by means of the transfer device by a distance equal to a distance between centers of adjacent ones of the plurality of rows of high-energy detectors, so that the detection device outputs data and an image of the object under inspection is reconstructed based on the outputted data, where N is a number of rows of the high-energy detectors.

Preferably, the image of the object under inspection is reconstructed based on the outputted data by computed tomography reconstruction.

In accordance with an aspect of the present invention, the high-energy detector assembly, and some low-energy detectors, superposed on the high-energy detectors of the high-energy detector assembly, of low-energy detectors of the low-energy detector assembly are configured to acquire a dual-energy CT image.

In accordance with an aspect of the present invention, the low-energy detector assembly is configured to acquire a low-energy CT image, and the high-energy detector assembly and some low-energy detectors, superposed on the high-energy detectors of the high-energy detector assembly, of low-energy detectors of the low-energy detector assembly are configured to acquire a dual-energy CT image, and a three-dimensional dual-energy CT image is acquired by fusing the low-energy CT image and the dual-energy CT image.

In accordance with an aspect of the present invention, the low-energy detector assembly comprises surface-array low-energy detectors.

The present invention proposes surface-array arrangement of low-energy detectors and sparse arrangement of high-energy detectors. As a result, detectors and data acquisition units are greatly reduced. A high-resolution three-dimensional CT image is acquired while high-accuracy hazardous article alarm is achieved. The cost of manufacture of the system is greatly decreased while high system performance is ensured.

DETAILED DESCRIPTION OF THE EMBODIMENTS

A further description of the invention will be made as below with reference to embodiments of the present invention taken in conjunction with the accompanying drawings.

Figure 1:
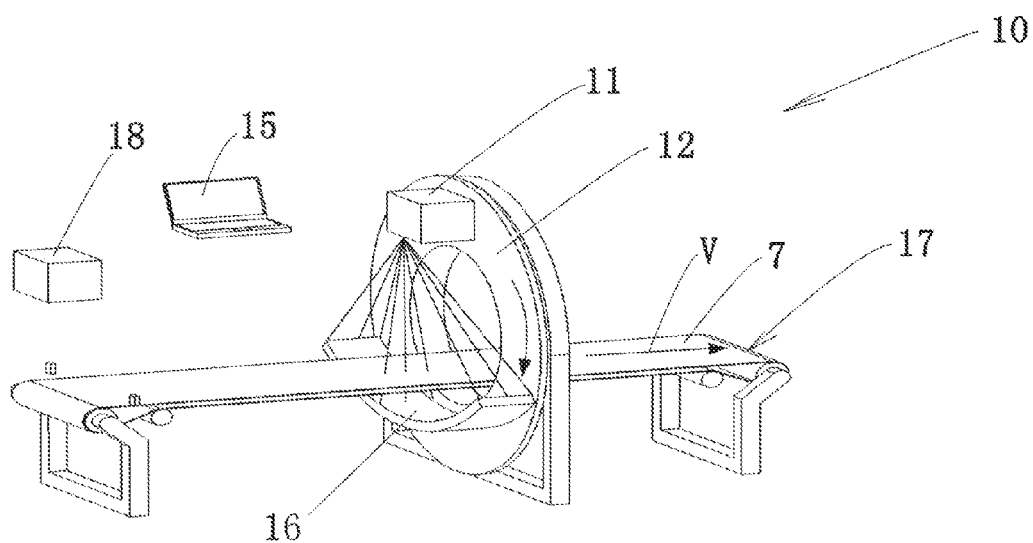
FIG. 1 is a schematic view of a CT system for safety inspection of baggage according to an embodiment of the present invention.
Figure 3:
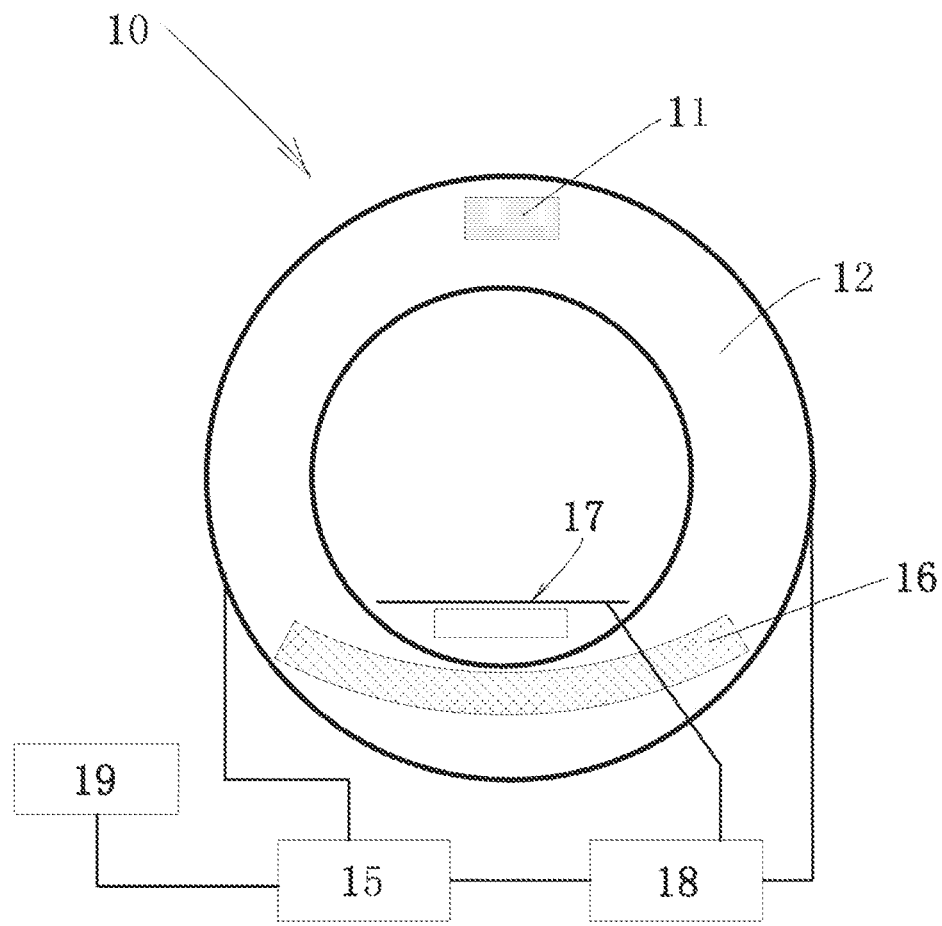
FIG. 3 is a schematic view of the CT system for safety inspection of baggage according to the embodiment of the present invention.

As shown in FIGS. 1 and 3, a CT system 10 according to an embodiment of the present invention comprises: a transfer device 17 for transferring an object under inspection in a transfer direction V; a gantry 12 rotatable about a rotational axis which may be substantially parallel to the transfer direction V; a ray source 11 connected to the gantry 12; a detection device 16 connected to the gantry 12 opposite the ray source 11 so that the detection device 16 and the ray source 11 can rotate together with the gantry 12, a control device 18 for controlling operation of the CT system 10; a data processing device 15 for processing data detected by the detection device 16; and an alarm device 19 for warning when there is a suspicious article in an object under inspection.

The ray source 11 may emit an X-ray. The ray source 11 may be an X-ray device, an accelerator, a radioisotope, or the like. The data processing device 15 may be a computer or the like. The data processing device 15 may be included in the control device 18.

Figure 2:
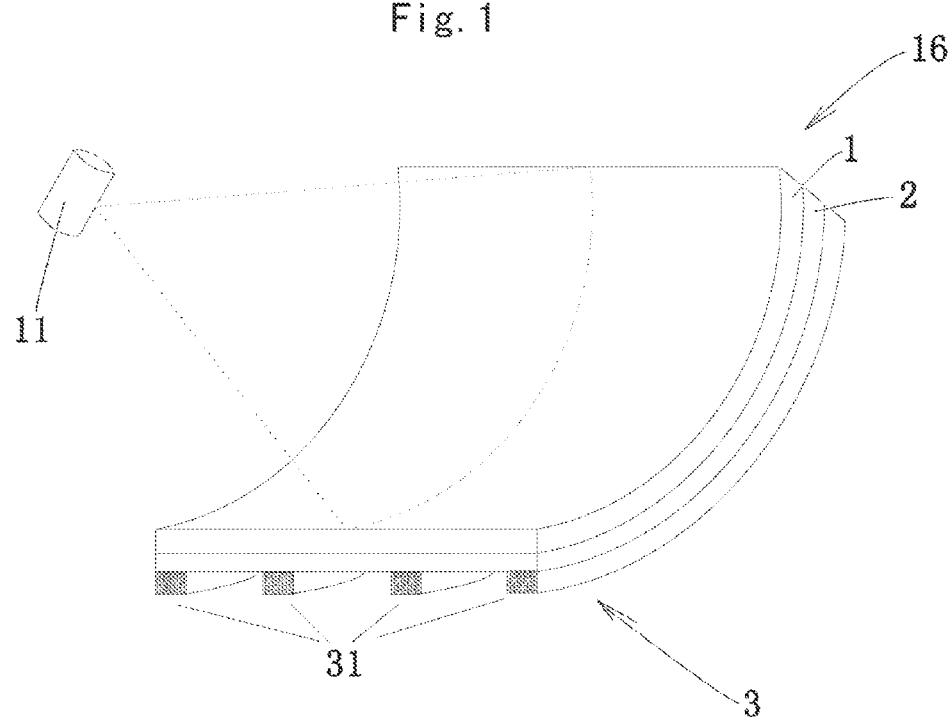
FIG. 2 is a schematic view of a detection device for a CT system according to an embodiment of the present invention.
Figure 4:
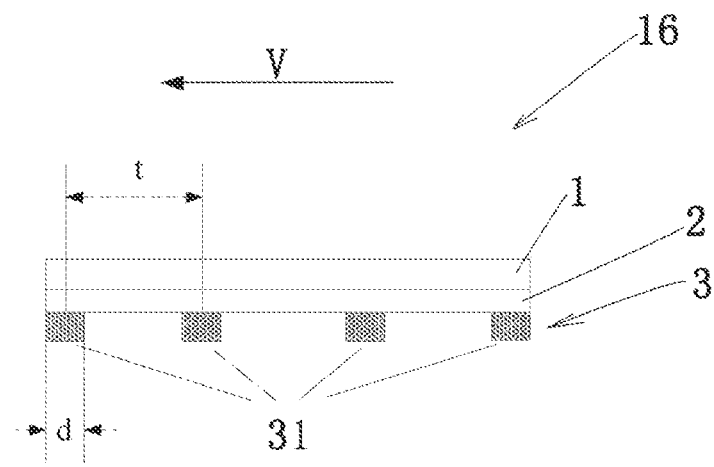
FIG. 4 is a schematic section view of the detection device for a CT system according to an embodiment of the present invention.

As shown in FIGS. 2 and 4, the detection device 16 comprises a low-energy detector assembly 1; and a high-energy detector assembly 3 disposed under the low-energy detector assembly 1.

As shown in FIGS. 2 and 4, the low-energy detector assembly 1 comprises surface-array low-energy detectors. The surface-array low-energy detectors are distributed substantially in a circular cylindrical surface. A central axis of the circular cylindrical surface passes substantially through a target point of the ray source 11, or is substantially parallel to a rotational axis of the gantry 12. Alternatively, a center of each of the surface-array low-energy detectors may be distributed in a circular arc. A center of the circular arc coincides with the target point of the ray source 11.

As shown in FIGS. 2 and 4, the high-energy detector assembly 3 comprises: a plurality of rows of high-energy detectors 31 arranged at predetermined intervals. The plurality of rows of high-energy detectors 31 are arranged substantially in the transfer direction V. A surface of each high-energy detector 31 facing towards the low-energy detector assembly 1 is located substantially in a circular cylindrical surface. A central axis of the circular cylindrical surface passes substantially through the target point of the ray source 11, or is substantially parallel to the rotational axis of the gantry 12. In addition, the plurality of rows of high-energy detectors may be arranged in any appropriate structure known in the art. The high-energy detector assembly, and some low-energy detectors, superposed on the high-energy detectors of the high-energy detector assembly, of low-energy detectors of the low-energy detector assembly are configured to acquire a dual-energy CT image. The low-energy detector assembly is configured to acquire a low-energy CT image, and a three-dimensional dual-energy CT image is acquired by fusing the low-energy CT image and the dual-energy CT image.

As shown in FIGS. 2 and 4, a filter 2 may be disposed between the low-energy detector assembly 1 and the high-energy detector assembly 3. A thickness of the filter is determined according to energy of the X-ray emitted by the ray source 11. The filter 2 absorbs a part of the energy of the ray to effectively increase a difference between energies detected by the high-energy detectors and the low-energy detectors. A material of the filter 2 may be copper, silver, or gold; or an alloy material containing copper, silver, or gold; or the like.

The low-energy detector and the high-energy detector may be made of the same scintillator material, or different scintillator materials. The scintillator material may be selected from one of CsI(Tl), CdWO4, GOS, ZnSe, and YAG.

Figure 5:
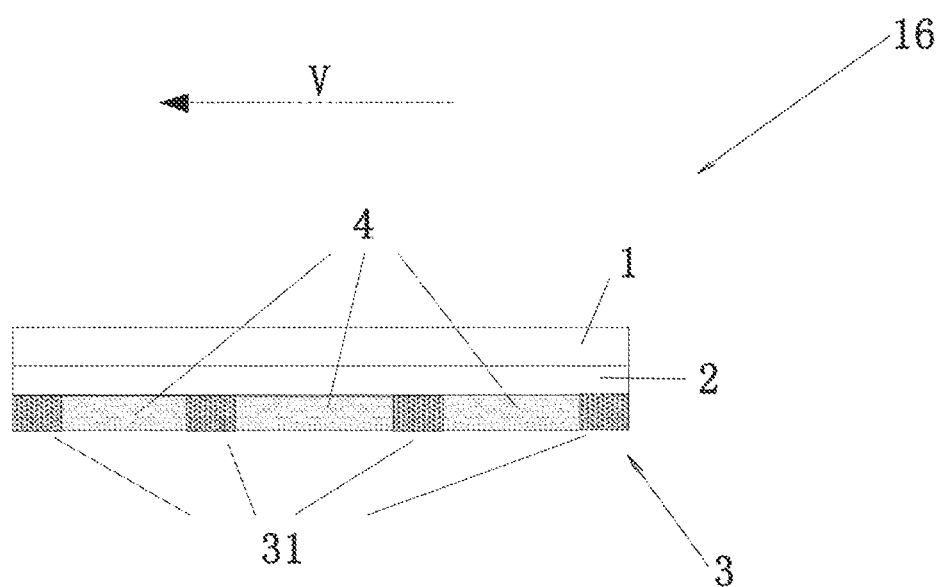
FIG. 5 is a schematic section view of the detection device for a CT system according to an embodiment of the present invention.

As shown in FIG. 5, in an embodiment of the present invention, the detection device 16 further comprises a member 4 disposed between adjacent ones of the high-energy detectors 31. The member 4 is made of a ray absorption material. For example, the member 4 is made of at least one of aluminum, iron, copper and lead, or an alloy of at least one of aluminum, iron, copper and lead. The member 4 may restrain scattered signals, and may function to shield radiation to some extent.

As shown in FIGS. 1 and 3, the transfer device 17 may comprise a belt 7 horizontally disposed. The gantry 12 rotates in a rotation plane which may be substantially perpendicular to a horizontal plane of the belt 7 or to the transfer direction V.

In the rotation plane of the gantry 12, the high-energy detectors and the low-energy detectors may be distributed in an arc shape, or may be distributed in such a way that a plurality of flat plate detectors as the high-energy detectors and the low-energy detectors are connected in an arc shape. The distribution of the high-energy detectors and the low-energy detectors in the rotation plane of the gantry may adopt various forms that meet the requirements of a scanning passage and a CT system.

Alternatively, the low-energy detector assembly 1 may comprise a plurality of rows of low-energy detectors arranged denser than the plurality of rows of high-energy detectors. The plurality of rows of low-energy detectors are arranged in the same direction as the plurality of rows of high-energy detectors, and corresponding ones of the low-energy detectors are superposed on each row of high-energy detectors.

During safety inspection, baggage is placed on the belt 7 to be moved horizontally while the gantry 12 rotates to rotate the ray source 11 and the detection device 16. The rotation axis of the gantry 12 may be parallel to a horizontal plane. The scanning of the baggage is configured to carry out a helical cone-beam scan. The control device 18 controls the action of the belt 7 and the gantry 12, the ray emission of the ray source 11, and the data acquisition of the detection device 16. The data processing device 15 obtains data detected by the detection device 16, processes the data, interoperates with a user, and informs the alarm device 19. The alarm device 19 is used for sending an alarm signal.

A high-resolution image can be acquired from the data detected by the surface-array low-energy detectors by reconstruction. The plurality of rows of high-energy detectors and the low-energy detectors superposed on the plurality of rows of high-energy detectors acquire dual-energy projection data together, and a CT image is acquired by the dual-energy projection data. The CT image may be a dual-energy CT image of a slice having a large thickness. High-energy and low-energy ray attenuation coefficient images, and information on an effective atomic member Z and a density D of the object under inspection can be accurately acquired by calculation through algorithm. According to distribution of a contraband item such as explosives and drugs in a plot of effective atomic member Z versus density D of the contraband item, the contraband item can be accurately judged. The entire CT system can acquire a high-resolution three-dimensional dual-energy CT image by fusing the high-resolution low-energy CT image and the dual-energy CT image of the slice having the large thickness. Based on the high-resolution image, the position of the contraband item such as explosives and drugs can be given, and the shape, size, and mass of the contraband item can be further obtained by analyzing. The CT system achieves comprehensive benefits of the high-resolution image, cost control and material identification.

The projection data acquired by the low-energy detectors can be processed by various reconstruction methods such as the FDK algorithm. The projection data acquired by the dual-energy detection device can be processed by various classical algorithms such as the iteration algorithm, the FDK algorithm or the computed tomography reconstruction. A substance is identified by a base material decomposition method or a double-effect decomposition method.

The CT system according to the present invention includes the following main functions:

1. the CT system can perform CT helical cone-beam scanning of an object such as baggage;
2. the CT system can acquire a high-resolution low-energy CT image of a slice and a three-dimensional image;
3. the CT system can acquire a dual-energy CT image of a slice having a large thickness;
4. the CT system can acquire a high-resolution dual-energy CT image by the image fusing method;
5. the CT system can reveal and identify a knife, a gun and the like according to the three-dimensional dual-energy CT image;
6. the CT system can acquire image data of the atomic member, density, high-energy and low-energy ray attenuation coefficients of baggage according to the dual-energy CT image data so as to be able to identify whether explosives, drugs and other contraband items are concealed in an object under inspection; and
7. the CT system can acquire the position, size, type, and weight estimate of explosives, drugs and other contraband items.

Specific operations of the high-energy detectors 31 of the CT system according to the present invention will be described below.

Assuming t represents a distance between centers of the two adjacent rows of high-energy detectors 31, N represents a number of the rows of high-energy detectors and N is an integer greater than 1, $r_0$ represents a rotary speed of a gantry, and s is a speed of a belt, a scanning manner can be designed to satisfy the following equation:

$$\frac{1}{Nr_0} = \frac{t}{s}$$

In an inspection area generated every time the gantry 12 rotates through 360 degrees, each row of high-energy detectors 31 inspect a sector section of 360/N degrees of the inspection area, and every time the gantry rotates through 360/N degrees, an object under inspection is moved by means of the transfer device 17 by a distance equal to the distance t between the centers of the two adjacent rows of high-energy detectors so that the sector sections of 360/N degrees are respectively inspected by the N rows of high-energy detectors 31 in a sequence from a first row of high-energy detectors of the N rows of high-energy detectors 31 on an upstream side in the movement direction V of the transfer device 17 to a last row of high-energy detectors of the N rows of high-energy detectors 31. Therefore, the detection device outputs data, and an image of the object under inspection can be reconstructed from the outputted data, for example by computed tomography reconstruction.

If an initial position of the first row of high-energy detectors 31 relative to the belt is set to $T_0$, then an initial position of the second row of high-energy detectors relative to the belt is set to $T_0-t$, an initial position of the third row of high-energy detectors relative to the belt is set to $T_0-2t$, and so on.

It can be easily found from the above equation that when the gantry 12 (that is, the detection device 31) rotates through 360/N degrees, the high-energy detectors 31 move a distance t in an axial direction of the gantry 12 relative to the moved object under inspection. Therefore, at this moment, the position of the first row of high-energy detectors becomes $T_0+t$, the position of the second row of high-energy detectors becomes $T_0$, the position of the third row of high-energy detectors becomes $T_0-t$, and so on. At this moment, the n+1$^{th}$ row of high-energy detectors are positioned at the same axial place where the n$^{th}$ row of high-energy detectors are located before the gantry 11 (that is, the detection device) rotates by 360/N degrees. Therefore, when the gantry rotates through 360 degrees, the N rows of high-energy detectors just cover 360 degrees from $T_0$ to $T_0+t_o$.

Theoretically, the dual-energy projection data acquired by the high-energy detectors and the low-energy detectors can be used for reconstruction by various reconstruction methods. As described above, when the gantry rotates through 360 degrees, the N rows of high-energy detectors just cover 360 degrees from $T_0$ to $T_0+t$. Therefore, the construction may be preferably carried out by the computed tomography reconstruction. The method is simple and fast.

As shown in FIG. 4, t represents the distance between the centers of the two adjacent rows of high-energy detectors in the transfer direction V of the belt 17, and d represents a width of the high-energy detectors 31 in the transfer direction V of the belt 17. The interval is equal to a difference between the center distance t and the width d. The interval between the adjacent rows of high-energy detectors 31 may be 5 to 80 mm, 10 to 70 mm, 20 to 60 mm, 30 to 50 mm, 35 to 45 mm, 36 to 40 mm, or 38 mm.

Since t>>d, where t represents the distance between the centers of the two adjacent rows of high-energy detectors of the detection device of the present invention, and d represents the width of the high-energy detectors, an area of a crystal of the high-energy detectors of the detection device is effectively decreased, thereby reducing the cost of the detection device. The detection rate of the detection device in the present invention is increased by multiple times compared with a detection device with a single row of detectors.

The CT system according to the present invention can fuse the low-energy CT image, the high-energy and low-energy ray attenuation coefficient images, the density image, and the atomic member image to present various images required by a user. The entire system can acquire a high-resolution three-dimensional dual-energy CT image by fusing the high-resolution low-energy CT image and the dual-energy CT image of the slice having the large thickness. High-accuracy identification of hazardous articles can be achieved by intelligent identification processing of the hazardous articles with the dual-energy CT image. In addition, high-resolution density and atomic member images may also be obtained by interpolation.

What is claimed is:

1. A detection device for a CT system comprising:
   a low-energy detector assembly having a thickness in a thickness direction; and
      a high-energy detector assembly disposed under the low-energy detector assembly,
      wherein the high-energy detector assembly comprises a plurality of rows of high-energy detectors arranged at predetermined intervals, and
      wherein the low-energy detector assembly comprises first low-energy detectors which coincide with the plurality of rows of high-energy detectors of the high-energy detector assembly when viewed in the thickness direction, and second low-energy detectors which do not coincide with the plurality of rows of high-energy detectors of the high-energy detector assembly when viewed in the thickness direction.

2. The detection device of claim 1, further comprising:
   a filter disposed between the low-energy detector assembly and the high-energy detector assembly.

3. The detection device of claim 1, wherein the CT system transfers an object under inspection in a transfer direction, and the plurality of rows of high-energy detectors are arranged substantially in the transfer direction.

4. The detection device of claim 1, wherein the low-energy detector assembly comprises surface-array low-energy detectors.

5. The detection device of claim 4, wherein the surface-array low-energy detectors are distributed substantially on a circular cylindrical surface.

6. The detection device of claim 1, wherein a surface of each high-energy detector facing towards the low-energy detector assembly is located substantially in a circular cylindrical surface.

7. The detection device of claim 1, wherein the predetermined intervals are from 5 mm to 80 mm.

8. The detection device of claim 1, wherein the predetermined intervals are from 30 mm to 50 mm.

9. The detection device of claim 1, further comprising: a member disposed between adjacent ones of the high-energy detectors.

10. The detection device of claim 9, wherein
    the member is made of a ray absorption material.

11. The detection device of claim 9, wherein
    the member is made of at least one of aluminum, iron, copper and lead, or an alloy of at least one of aluminum, iron, copper and lead.

12. The detection device of claim 1, wherein the high-energy detector assembly and the first low-energy detectors of the low-energy detector assembly are configured to acquire a dual-energy CT image.

13. A CT system, comprising:
    a transfer device for transferring an object under inspection in a transfer direction;
    a gantry;
    a ray source connected to the gantry; and
    the detection device of claim 1 connected to the gantry opposite the ray source.

14. The CT system of claim 13, wherein the plurality of rows of high-energy detectors are arranged substantially in the transfer direction.

15. The CT system of claim 14, wherein every time the gantry rotates through 360/N degrees, an object under inspection is moved by means of the transfer device by a distance equal to a distance between centers of adjacent ones of the plurality of rows of high-energy detectors, where N is a number of rows of the high-energy detectors.

16. The CT system of claim 14, wherein every time the gantry rotates through 360/N degrees, an object under inspection is moved by means of the transfer device by a distance equal to a distance between centers of adjacent ones of the plurality of rows of high-energy detectors, so that the detection device outputs data and an image of the object under inspection is reconstructed based on the outputted data, where N is a number of rows of the high-energy detectors.

17. The CT system of claim 16, wherein the image of the object under inspection is reconstructed based on the outputted data by computed tomography reconstruction.

18. The CT system of claim 13, wherein the high-energy detector assembly and the first low-energy detectors of the low-energy detector assembly are configured to acquire a dual-energy CT image.

19. The CT system of claim 13, wherein the low-energy detector assembly is configured to acquire a low-energy CT image, the high-energy detector assembly and the first low-energy detectors of the low-energy detector assembly are configured to acquire a dual-energy CT image, and a three-dimensional dual-energy CT image is acquired by fusing the low-energy CT image and the dual-energy CT image.

20. The CT system of claim 19, wherein the low-energy detector assembly comprises surface-array low-energy detectors.

* * * * *

UNITED STATES PATENT AND TRADEMARK OFFICE
CERTIFICATE OF CORRECTION

PATENT NO. : 9,572,540 B2  
APPLICATION NO. : 14/355175  
DATED : February 21, 2017  
INVENTOR(S) : Li Zhang et al.

Page 1 of 1

It is certified that error appears in the above-identified patent and that said Letters Patent is hereby corrected as shown below:

On the Title Page

<u>Item (72):</u>
The correct inventors are, in order, --Li Zhang, Beijing (CN); Zhiqiang Chen, Beijing (CN); Qingping Huang, Beijing (CN); Yunda Sun, Beijing (CN); Xin Jin, Beijing (CN); Le Shen, Beijing (CN); Yuxiang Xing, Beijing (CN); Hu Tang, Beijing (CN); Yuanjing Li, Beijing (CN); Mingzhi Hong, Beijing (CN); Jinning Liang, Beijing (CN); Qianlu Ren, Beijing (CN); Liang Li, Beijing (CN); Hui Ding, Beijing (CN); Ming Chang, Beijing (CN)--

Signed and Sealed this  
Fourth Day of September, 2018

Andrei Iancu  
*Director of the United States Patent and Trademark Office*